US00PP09040P

United States Patent [19]

Larson

[11] Patent Number: Plant 9,040

[45] Date of Patent: Jan. 10, 1995

[54] TABLE GRAPE VARIETY NAMED MARIAH

[76] Inventor: Drake Larson, P.O. Box 355, Thermal, Calif. 92253

[21] Appl. No.: 134,258

[22] Filed: Oct. 8, 1993

[51] Int. Cl.[6] ..... A01H 5/00

[52] U.S. Cl. ..... Plt./47.1

[58] Field of Search ..... Plt. 47.1

*Primary Examiner*—James R. Feyrer

*Attorney, Agent, or Firm*—Christie, Parker & Hale

[57] ABSTRACT

A new and distinct variety of grapevine producing early maturing black seedless table quality grapes which are firm and large with no splitting.

3 Drawing Sheets

BACKGROUND OF THE INVENTION

The invention relates to a new and distinct variety of the vinifera species which produces early maturing black seedless table grapes. The varietal denomination of the new variety is Larson D-12; however, it will be identified commercially as Mariah.

The new variety is the result of a cross of two unnamed, unpatented seedlings of my creation and was one of over 800 such seedlings grown near Thermal, Calif. and brought to fruiting, evaluated and asexually reproduced.

The variety of black seedless grape known as 'Beauty' (unpatented) has been considered the earliest fruiting black seedless grape produced for the commercial market. However, the fruit of 'Beauty' is soft and oes not hold in storage well. Another commerical variety, 'Fantasy', tends to crack and is low yielding and matures relatively late.

SUMMARY OF THE INVENTION

The new variety, 'Mariah', is an early maturing black seedless grape which is firmer than 'Beauty', earlier fruiting, and more productive than the variety 'Fantasy'. 'Larson D-12' is also suitable for drying into raisins. In addition, no Gibb is required for sizing and the new variety is low-labor intensive compared to the varieties 'Beauty' and 'Fantasy'. In the culture of the new variety GA is not applied, and may even be phytotoxic. The new variety is quadrilateral cordon pruned and singal spurred because of the youth of the plants. Berry pruning is not required for attainment of berry size. The variety "Fantasy" is cane pruned whereas the new variety and the variety "Beauty" are cordon pruned.

The new variety is similar to, but the distinguishable from companion variety "Larson B-36" which is the subject of U.S. patent application Ser. No. 08/134257, filed Oct. 8, 1993. The new variety is somewhat less vigorous than the variety "Larson B-36" and fruits somewhat earlier, e.g., about four days, in a desert climate. The bud break of the new variety is earlier than "Larson B-36" and similar to "Beauty" Seedless whereas "Larson B-36" is between "Beauty" and "Thomson" Seedless. "Larson B-36" tends to attain longer growth at maturity than the new variety and the trunk diameter is smaller. The canopy of the variety "Larson B-36" is considerably denser than the canopy of the new variety. The seed traces for both varieties are the same and the juice and raisins of the new variety have not been observed. The adhesion of the skin to the flesh is similar to "Thomson" Seedless in the strength of attachment of the berry, to the pedicles is strong for fresh and stored fruit.

The number of berries per cluster is about 60 to 250 and the new variety produces 50 to 90 clusters per plant. It is usually desirable to leave about 30 to 40 clusters per plant for optimum fruit quality. The tendrils tend to be straight to slightly curly and without support will curl more. The internode length varies greatly according to fertilizer and water availability but is generally from 2 to 5 inches.

Bark texture is not significantly different from other varieties and the foliage color will vary. The foliage has three major holes and three minor holes and the sinus is similar to 'Flames' seedless, with an irregularly serrate and coarse margin. The color of the berries is evident from the illustrations and variety is self-fertile.

Among the novel characteristics possessed by this new variety which distinguish it from its parents and all other varieties of which I am aware are its firm, large berries, improved flavor, early maturity and absence of splitting. Fruiting is best when plants are spur (two bud) pruned.

Asexual reproduction by rooted cutttings of the new variety as performed in Thermal, Calif. shows that the foregoing and other distinguishing characteristics come true to form and are established and transmitted through succeeding propagations.

BRIEF DESCRIPTION OF ILLUSTRATION

The accompanying illustrations shown typical specimens of the vegetative growth and berries of the new vareity depicted in color as nearly true as it is reasonably possible to make the same in a color illustration of this character.

In the drawings, one view illustrates a bunch of grape berries of the new variety, another illustration depicts the vine of the new variety, a third illustration shows the foliage of the new variety and a fourth illustration describes a closer view of the bunches. The remaining two illustrations show tendrils and growth of the new variety, and a leaf.

DETAILED DESCRIPTION OF THE NEW VARIETY

Parentage: Seedling.

*Seed parent.*—Unnamed seedling.

*Pollen parent.*—Unnamed seedling.

Species: Vinifera, black seedless.

The following is a detailed description of specimens of the new variety grown in Thermal, Calif. in the month of June, 1993. The color terminology used is in accordance with The Royal Horticultural Society Colour Chart (R.H.S.C.C.), and refers to plate numbers in the aforementioned color chart. Phenotypic expression may vary depending on environmental, climate and cultural conditions. Where general description terms such as average, normal and medium are used, it is intended that characteristics so described are not considered distinguishing.

VINE

A. *Size (general)*: Very vigorous (much more vigorous than 'Beauty').
B. *Form*: Condor (quadrilateral).
C. *Vigor*: Very vigorous.
D. *Time of sprouting:* Early February, in 1993.
E. *Productivity:* Heavy yielder.
F. *Trunk*:
  (1) *Trunk diameter.*—About 5 cm at 28 months generally round.
  (2) *Bark (color).*—Light brown texture-striated, similar to 'Thompson', 'Pearlette' and 'Flame'.
G. Canes:
  (1) *Size.*—Average similar to 'Thompson'.
  (2) *Number.*—About 17–22.
  (3) *Diameter.*—Average similar to 'Thompson'.
  (4) *Color.*—Light brown.
  (5) *Form.*—Varies from plant to plant until mature, and similar to 'Thompson', 'Pearlette' and 'Flame'.
  (6) *Nodes (generally).*—Present.
  (7) *Nodes (size).*—Medium.
  (8) *Internodes (size).*—Average.
  (9) *Internode length.*—About 7.5 to 10.2 cm.
  (10) *Number of tendrils.*—Normal.
  (11) *Tendril thickness.*—Average.
  (12) *Tendril length.*—Average, variable, as shown in accompanying illustration.
  (13) *Tendril form.*—Straight to mild spiral.
  (14) *Tendril texture.*—Average as shown in attached illustration.
H. Flowers: Fertile with upright stamens.
  *Date of bloom.*—Early April, in 1993, in Thermal, Calif., flowers have stamens, pistils and produce plllen; self fertile, blooming starts before 'Beauty' and before 'Larson B-36'.

FOLIAGE

A. Size: Medium.
B. Average length: Medium, about 1 to 15 cm long from the point of attachment of the leaf petiole to the tip of the leaf.
C. Average width: Medium about 2 to about 10 cm from widest point of two widest lobes of the leaf.
D. Thickness: Average.
E. Form: Average generally round.
F. Color
  (1) *Dorsal surface.*—Light green near 146C to 146D.
  (2) *Ventral surface.*—Light green near 146D.
G. Texture
  (1) *Dorsal surface.*—Relatively smooth.
  (2) *Ventral surface.*—Relatively smooth.
H. Number of lobes: Variable.
I. Terminal lobe:
  Form.—Variable.
J. Shoot tip: Similar to 'Flame' seedless.
K. Shoot: Moderately vigorous.
L. Leaf blade: Average.
M. Density: Moderate, less than 'Flame' and more dense than 'Beauty'.
N. Sinus: Similar to 'Thompson' seedless
O. Margins: Irregularly serrate and coarse.

FRUIT

A. Maturity at time of description: Late May, in 1993.
B. Ripening date: Same as maturity starts ripening before 'Beauty'.
C. Storage quality: Very good for desert; over 3 weeks.
D. Shipping quality: Very good; maintains integrity of berries without cracking; firm skin and flesh; withstands long transit times, e.g. 2 weeks, without damage.
E. Cluster:
  (1) *General description.*—Well filled, long.
  (2) *Size.*—About 0.4 to 0.9 kg.
  (3) *Length.*—Medium.
  (4) *Natural cluster length.*—About 23 cm.
  (5) *Cluster form (shape).*—Elongated.
  (6) *Peduncle.*—Length: About 3.8 cm. Thickness: Average.
  (7) Pedicel length.—About 0.8 cm.
F. Berry:
  (1) *Berry length (natural vines).*—Varies but averages about 2 to 2.4 cm.
  (2) *Berry diameter.*—Varies but averages about 2 to 2.2 cm.
  (3) *Berry weight.*—About 3.8 to 6.1 g; average about 4.8 g.
  (4) *Uniformity.*—Very.
  (5) *verry color.*—Nominally black; slight blue red near to between 183A and 53 A.
  (6) *Bloom.*—Similar to 'Thompson', less than 'Beauty'.
  (7) *Skin.*—Thickness: Medium, skin well attached, better than 'Thompson' and 'Beauty', similar to 'Pearlette'. Texture: Firm.
  (8) *Brush.*—Brush is retained on pedicel.
G. Flesh:
  (1) *Appearance (general).*—Translucent, light color, aroma similar to 'Pearlette', 'Thompson' and 'Flame', flesh is well attached to skin, better than 'Thompson' and 'Beauty' and similar to 'Pearlette'
  (2) *Texture.*—Firm, surface bloom similar to 'Thompson', less than 'Beauty' and more than 'Flame'.
  (3) *Flavor.*—Very sweet; slight plum flavor.
  (4) *Quality.*—Very good.
H. Seeds: Seedless.
I. Use: Table grape, juice characteristics not determined.
J. Uniqueness: Earlier fruiting than 'Fantasy' under similar growing conditions; shows no signs of cracking or splitting.
K. Disease and insect resistance: Average resistance to leaf hopper and thrip; good resistance to nematodes; good resistance to disease (no disease observed).

I claim:

1. A new and distinct black seedless grape plant known as 'Larson D-12', substantially as shown and described.

* * * * *

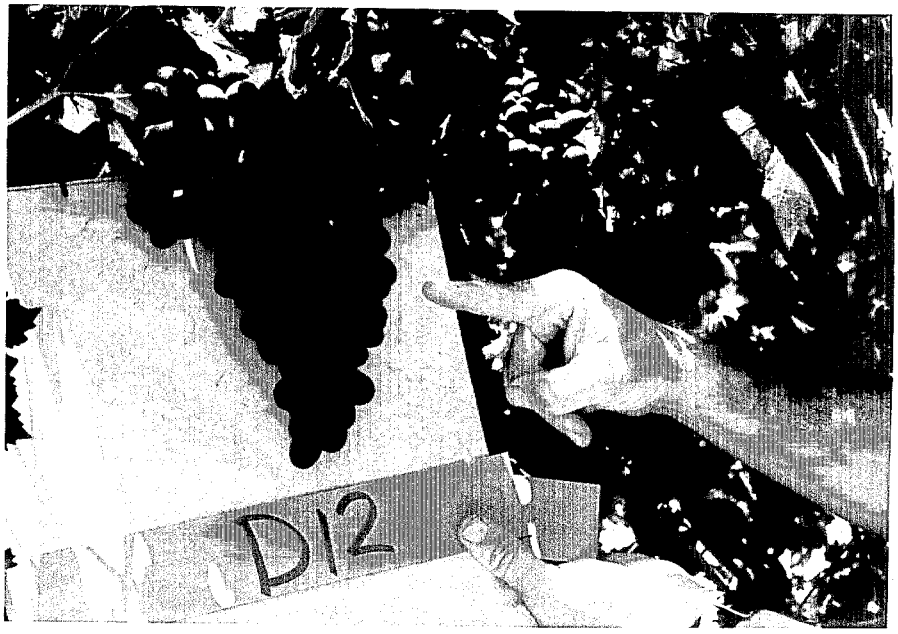
D12
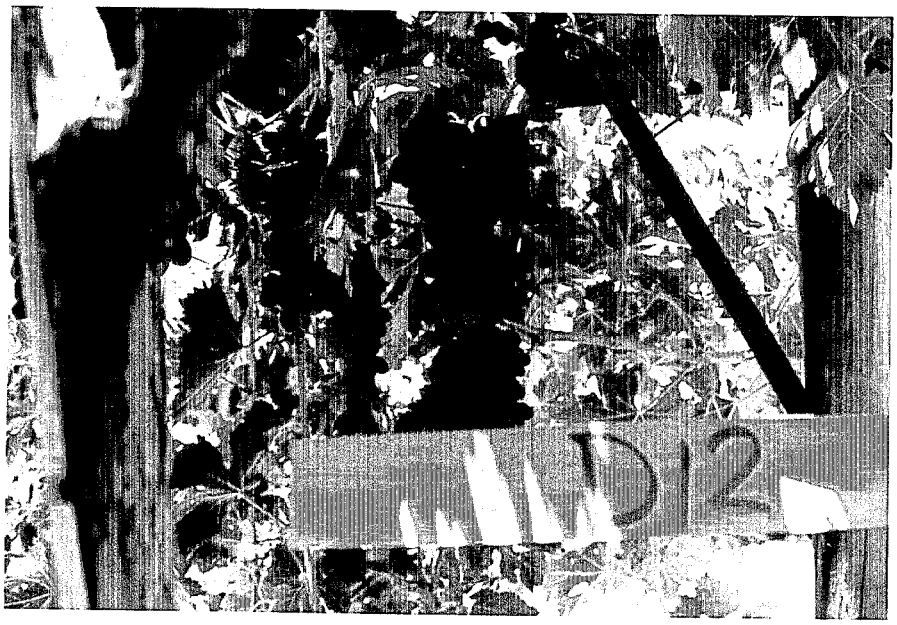
D12

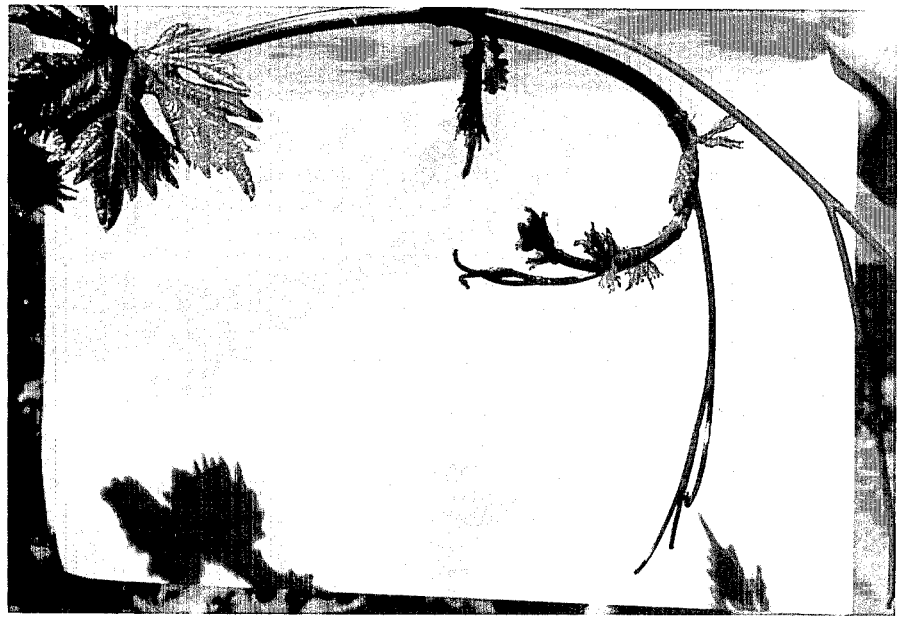
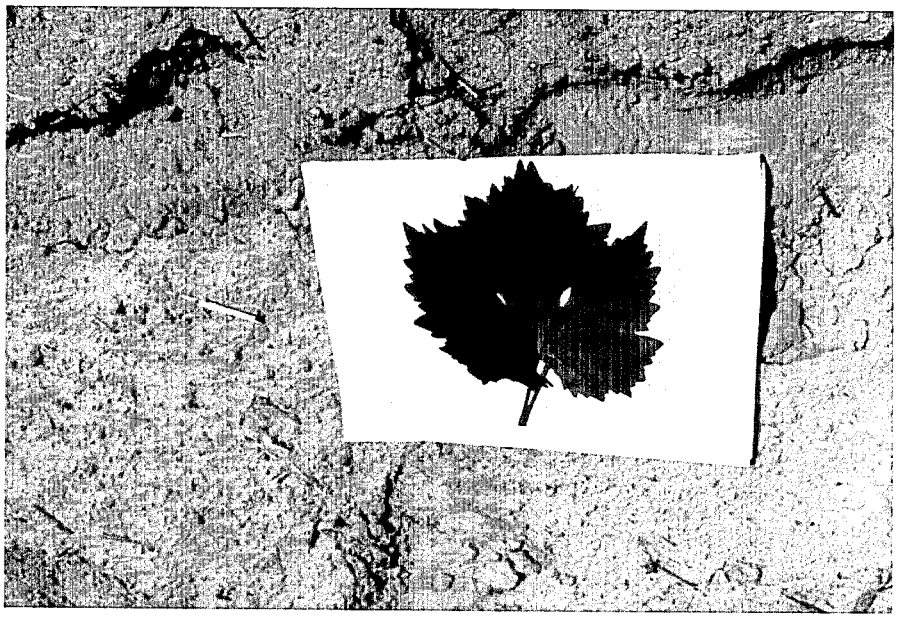

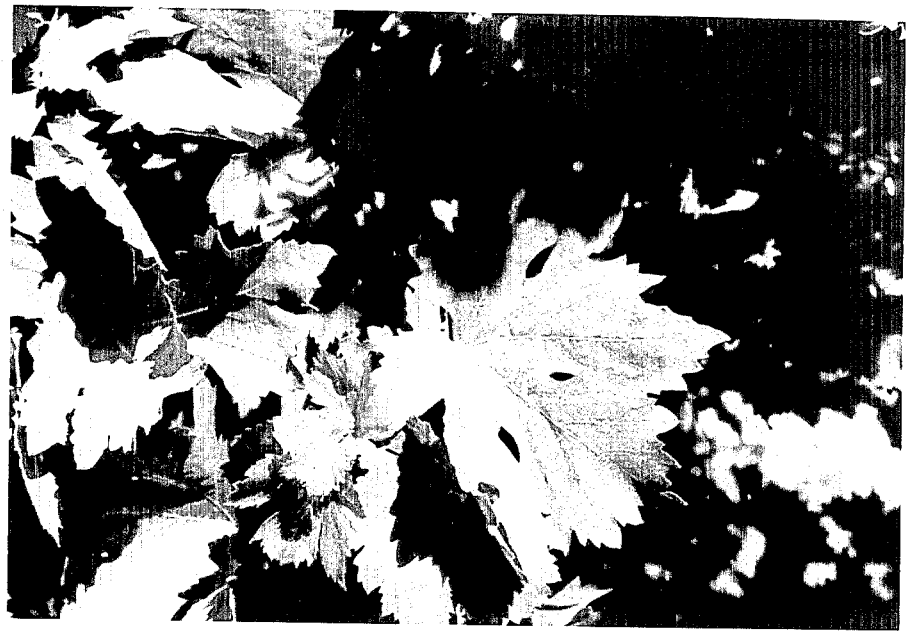
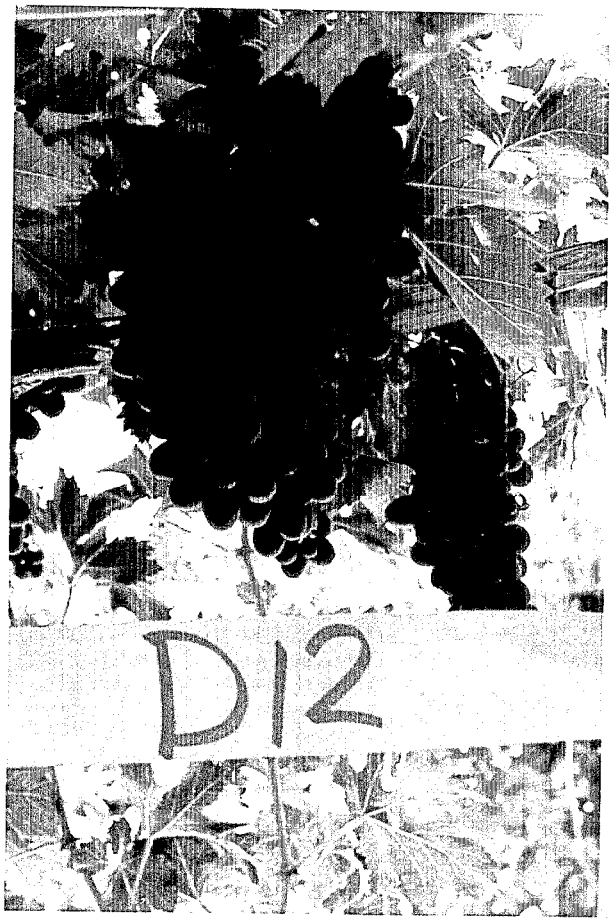
D12